(12) United States Patent
Dugand et al.

(10) Patent No.: US 11,577,031 B2
(45) Date of Patent: Feb. 14, 2023

(54) AUTOMATIC INJECTION DEVICE WITH IMPROVED SYRINGE RETENTION

(71) Applicant: Nemera La Verpillière, La Verpilliere (FR)

(72) Inventors: Pascal Dugand, Estrablin (FR); Kevin Stamp, Sheffield (GB)

(73) Assignee: Nemera La Verpillière

( * ) Notice: Subject to any disclaimer, the term of this patent is extended or adjusted under 35 U.S.C. 154(b) by 247 days.

(21) Appl. No.: 16/325,987

(22) PCT Filed: Jun. 16, 2017

(86) PCT No.: PCT/FR2017/051565
§ 371 (c)(1),
(2) Date: Feb. 15, 2019

(87) PCT Pub. No.: WO2018/033667
PCT Pub. Date: Feb. 22, 2018

(65) Prior Publication Data
US 2020/0155769 A1     May 21, 2020

(30) Foreign Application Priority Data
Aug. 16, 2016  (FR) ...................................... 1657764

(51) Int. Cl.
*A61M 5/32*    (2006.01)
*A61M 5/20*    (2006.01)

(52) U.S. Cl.
CPC ............ *A61M 5/3202* (2013.01); *A61M 5/20* (2013.01); *A61M 5/2033* (2013.01); *A61M 5/3204* (2013.01); *A61M 5/3245* (2013.01); *A61M 2005/2073* (2013.01)

(58) Field of Classification Search
CPC .... A61M 5/20; A61M 5/2033; A61M 5/3202; A61M 5/3204; A61M 5/3213; A61M 2005/2073; A61M 5/3243; A61M 5/3245
See application file for complete search history.

(56) References Cited

U.S. PATENT DOCUMENTS

| 8,734,402 B2 | 5/2014 | Sharp et al. |
| 2010/0185148 A1 | 7/2010 | Gillespie, III et al. |

FOREIGN PATENT DOCUMENTS

| GB | 2478349 A | 9/2011 |
| WO | 2009081103 A1 | 7/2009 |
| WO | 2009081133 A1 | 7/2009 |
| WO | 2011012849 A1 | 2/2011 |

*Primary Examiner* — Shefali D Patel
(74) *Attorney, Agent, or Firm* — St. Onge Steward Johnston & Reens LLC

(57) ABSTRACT

An automatic injection device includes an end sleeve and a syringe support mounted slidably with respect to the end sleeve. The syringe support is intended to carry an injection syringe provided with an injection needle and with a cap for protecting the injection needle. The automatic injection device includes a membrane formed by at least two locking elements which are mounted so as to slide substantially radially in the end sleeve between a configuration permitting passage of the cap for protecting the injection syringe, in which configuration limit stops of the at least two locking elements, intended to cooperate with a shoulder of the injection syringe, are moved away from each other, and a configuration permitting immobilization of the injection syringe, in which configuration the limit stops of the at least two locking elements are moved towards each other.

11 Claims, 7 Drawing Sheets

AUTOMATIC INJECTION DEVICE WITH IMPROVED SYRINGE RETENTION

FIELD OF THE INVENTION

This invention relates to the field of automatic injection devices for liquids, especially pharmaceutical liquids.

BACKGROUND OF THE INVENTION

An automatic injection device is generally a medical device used for automatic administration of a liquid medication requiring an injection. These devices allow in particular persons, for example suffering from rheumatoid arthritis, multiple sclerosis, diabetes or undergoing an anaphylactic shock in case of allergy, to inject themselves a dose of medication independently.

An example of an automatic injection device is described in document U.S. Pat. No. 8,734,402. The device comprises an injection syringe which contains the liquid product to be injected and which is provided with a needle and a syringe support. It is generally sufficient to press the device briefly on the patient's skin to initiate a penetration of the needle into the skin, followed by an injection of the liquid, then retraction of the needle inside the device to prevent the needle from injuring anyone.

SUMMARY OF THE INVENTION

More precisely, the device comprises a syringe support configured to house the injection syringe, so that it is fixedly mounted in the syringe support throughout the operation of the device. This syringe supports consists of two semi-tubular half-shells, assembled together when the injection syringe is fitted inside, so as to form a tubular shell around the syringe.

The injection syringe comprises a collar at one of its ends and a cap for protecting the needle, for example a Rigid Needle Shield (RNS), at its other end. The diameter of the protective cap is often greater than that of the syringe body.

The syringe support housing the syringe has a generally tubular shape whose inner diameter is close to the outer diameter of the central part of the syringe. It is not always possible to insert the syringe in the syringe support once the two half-shells forming it have been assembled, since the collar and the cap are larger than the central part of the syringe and therefore larger than the inner diameter of the syringe support. Generally, however, the injection syringe is assembled in the automatic injection device by a pharmaceutical laboratory and not by the manufacturer of the automatic injection device, such that if the assembly of the injection syringe in the automatic injection device is simplified in any way, the pharmaceutical laboratory does not need to acquire complex apparatus.

The invention aims in particular to provide an automatic injection device wherein the assembly of the injection syringe in the automatic injection device is simplified.

This invention therefore relates to an automatic injection device comprising:
an end sleeve
a syringe support slidably mounted relative to the end sleeve, the syringe support being intended to carry an injection syringe provided with an injection needle and with a cap for protecting this injection needle,
characterised in that it comprises a membrane formed by at least two locking elements which are mounted so as to slide substantially radially in the end sleeve between a configuration permitting the passage of the cap for protecting the injection syringe, in which configuration limit stops of the locking elements, intended to cooperate with a shoulder of the injection syringe, are moved away from each other, and a configuration permitting the immobilisation of the injection syringe, in which configuration the limit stops of the locking elements are moved towards each other.

Thus, since the membrane can be in a configuration permitting the passage of the protective cap, the injection syringe carrying the protective cap can be assembled in the part of the injection device by inserting the injection syringe axially from one end of the syringe support, the protective cap being inserted first. Consequently, it is no longer necessary to assemble the syringe support after positioning the injection syringe and the two half-shells forming the syringe support can therefore be assembled before introducing the injection syringe therein or using a syringe support which is not composed of two half-shells.

In addition, when the injection syringe is held by the collar, the axial forces related to the injection must be limited since the collars are not strong enough to withstand high forces. In this invention, however, the membrane can be configured to hold the injection syringe by a shoulder of this syringe located at the base of the injection syringe needle. In this configuration, the axial forces on the injection syringe are not transmitted to the collar located at the end of the syringe body opposite the needle. It therefore becomes possible to consider using particularly stiff springs, and therefore inject a product of high viscosity. In particular, an injection spring having a force in compressed position of 20 newtons, even 50 newtons or even 80 newtons or more can be used. It will be understood that an injection syringe not provided with a collar could also be used, or that the injection syringe could take the shape of a cartridge for reception of the liquid.

According to other optional characteristics corresponding to different embodiments of the injection device:
the locking elements comprise flexible non-return tabs intended to prevent the locking elements from being withdrawn from the injection device by cooperating with the end sleeve;
the locking elements are provided with projecting surfaces intended to rub against complementary surfaces of the end sleeve to prevent the locking elements from moving prematurely from their passage configuration to their immobilisation configuration;
the end sleeve is fixed to a distal end of a "control" member of generally tubular shape, in which the syringe support slides, this control member being mounted telescopically in an outer casing, the relative movement of the control member with respect to the outer casing controlling actuation of the automatic injection device;
the locking elements are provided with ramps intended to cooperate with the outer casing to move from their passage configuration to their configuration immobilising the injection syringe;
pins are mounted slidably in the control member, these pins being forced, by pin return means, to press on respective surfaces of the locking elements in which hollows are formed so as to create hard points retaining the locking elements in their passage or immobilisation configuration;
the return means are housed between respective surfaces of the syringe support and respective shoulders of the pins so as to elastically return the syringe support to the proximal end of the control member;

- the control member and the outer casing comprise non-return locking means, preventing the control member from sliding relative to the outer casing in one direction;
- the non-return locking members comprise a tab of the control member cooperating with notches formed in the outer casing;
- the limit stops of the locking elements are partly defined by convex surfaces of these locking elements;
- the injection syringe intended to be carried by the syringe support comprises a syringe body provided with a distal end carrying the injection needle, the shoulder of the injection syringe against which the limit stops of the locking elements are intended to cooperate defining the proximal end of the injection needle.

BRIEF DESCRIPTION OF THE DRAWINGS

The invention will be better understood on reading the following description, given solely by way of example and with reference to the accompanying drawings in which:

FIGS. 7 and 8 show the injection device in an actuated configuration, before injection, FIGS. 9 and 10 show the injection device in a configuration after injection, before retraction of the injection needle, FIGS. 11 and 12 show the injection device in a configuration after retraction of the injection needle;

DETAILED DESCRIPTION OF THE INVENTION

FIGS. 1 to 12 show an automatic injection device 13 according to the invention. This automatic injection device 13 has a general shape of revolution about the axis X. This automatic injection device 13 is intended to be manually grasped at one end, which will be referred to subsequently as the proximal end. The opposite end, which will be referred to as the distal end, is intended to be applied against a patient's skin, on an injection area.

Figure 4:
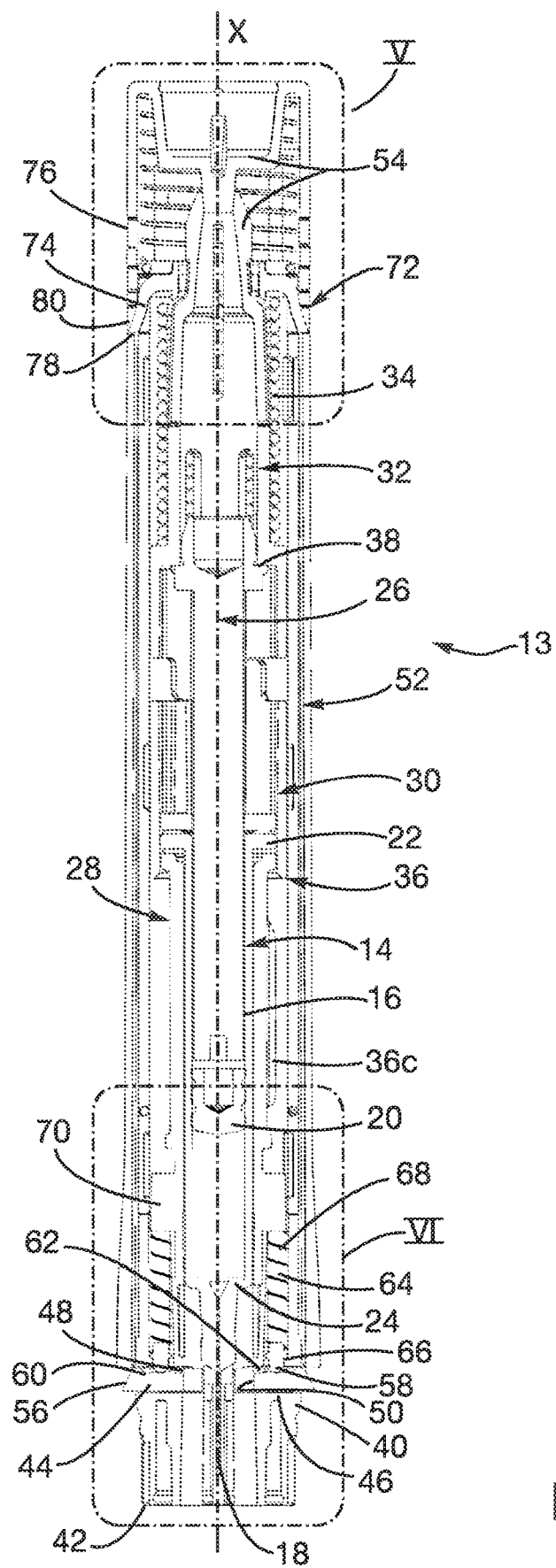
FIG. 4 is a cross-sectional view respectively along plane IV-IV of FIG. 1.

The automatic injection device 13 is intended to be provided with an injection syringe 14, shown in particular on FIG. 4. In this first embodiment of the invention, the injection syringe 14 is an injection syringe 14 made of glass comprising a syringe body 16 of generally tubular shape of axis X containing a pharmaceutical liquid, which may be relatively viscous, to be injected into the patient's body.

The distal end of the syringe body 16 is provided with an injection needle 18. A piston 20 is mounted slidably in the syringe body 16 so that when the piston 20 moves towards the distal end of the syringe body 16, the pharmaceutical liquid contained in the syringe body 16 is ejected through the injection needle 18.

To actuate the automatic injection device 13, the user presses the distal end of the end sleeve 40 on the injection area and presses the automatic injection device 13 briefly against this area. Thus, the control member 36 retracts into the outer casing 32 and means for actuating the device 34, carried by one of the command members 32 and the control member 36, cooperate to actuate the automatic injection device 13.

At its proximal end, the syringe body 16 comprises a radial collar 22. At its distal end, the syringe body 16 comprises a distal shoulder 24.

A piston rod 26, shown on FIG. 4, is in contact with a proximal end of the piston 20. This piston rod 26 is intended to push the piston 20 towards the distal end of the syringe body 16 when injecting the pharmaceutical product into the patient's body.

Figure 1:
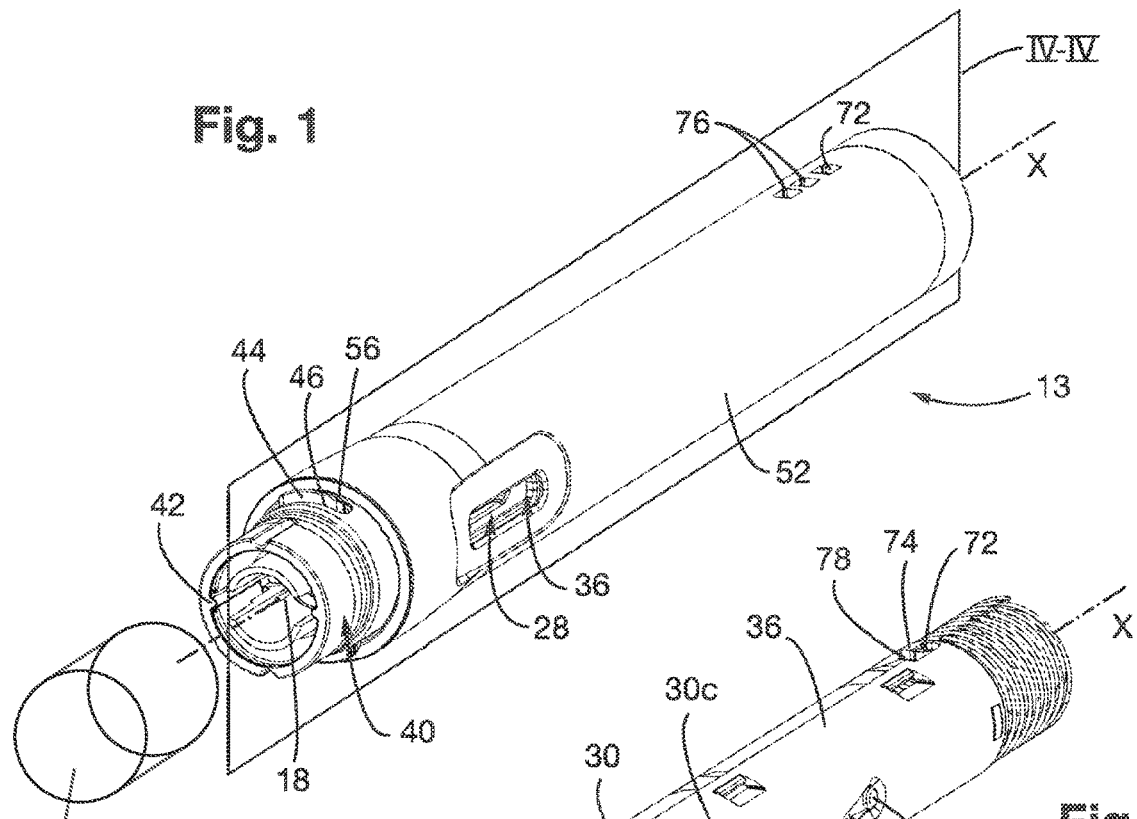
FIG. 1 is a perspective view of an automatic injection device according to a first embodiment of the invention, in an initial configuration, before the operation of this automatic injection device.
Figure 2:
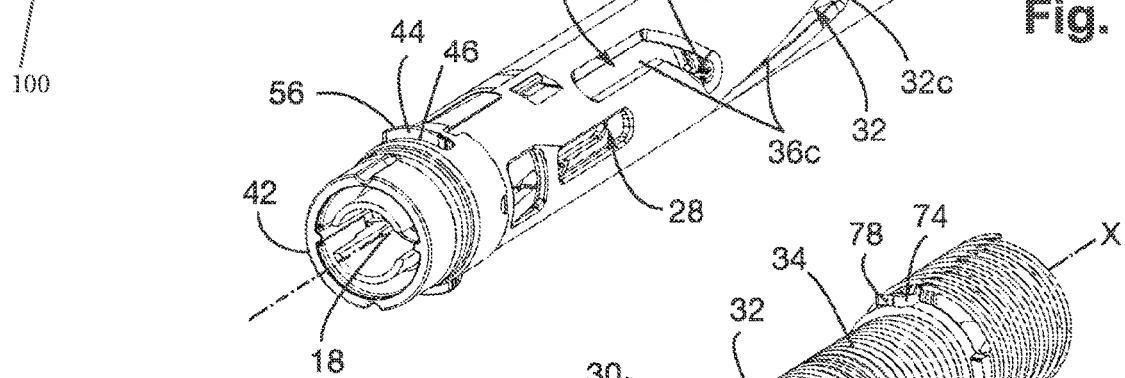
FIG. 2 is a view similar to FIG. 1, the automatic injection device being shown without an outer casing.
Figure 3:
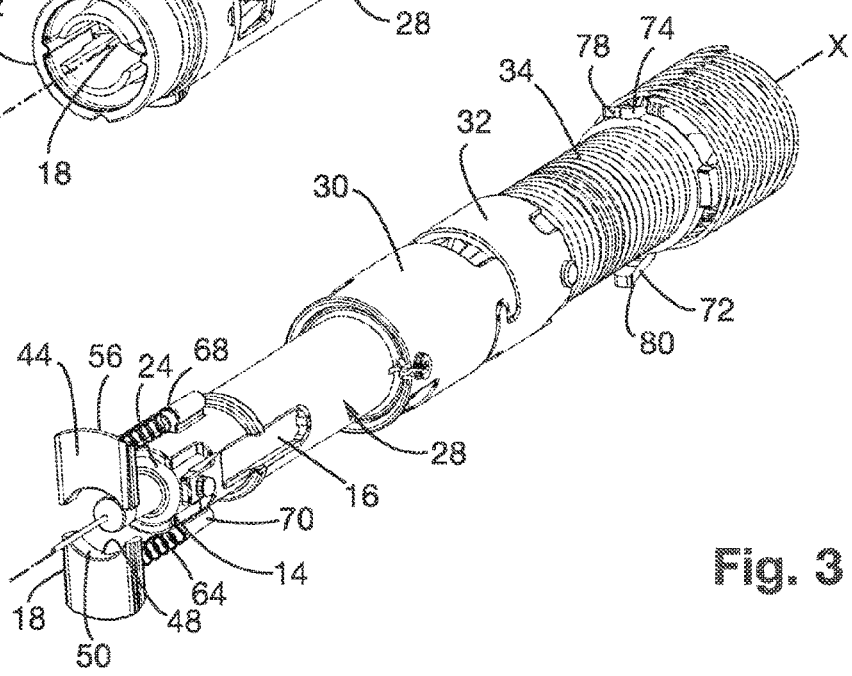
FIG. 3 is a view similar to FIG. 2, the injection device being shown with neither control member nor end sleeve.

The automatic injection device 13 comprises a syringe support 28, shown in particular on FIGS. 3 and 4, for carrying the injection syringe 14. The syringe support 28 has a generally tubular shape of axis X comprising an opening at the distal end and at the proximal end.

Command members 30, 32 are positioned on the proximal end of the syringe support 28. These command members 30, 32 are intended to cooperate with each other and with the syringe support 28 and the piston rod 26. By cooperating, the command members 30, 32 perform the following steps:

- firstly, the command members 30, 32 push the syringe support 28 so that the injection needle 18 is inserted into the patient's skin,
- the command members 30, 32 then push the piston rod 26 and the piston 20 in the syringe body 16 to inject the pharmaceutical product,
- lastly, the command members 30, 32 release the piston rod 26 and the syringe support 28 axially so that they can move back to allow the injection needle 18 to retract, leave the patient's skin and be inaccessible.

The command members 30, 32 are pushed by an injection spring 34 located in the distal end of the automatic injection device 13.

The syringe support 28 and the command members 30, 32 are mounted slidably in a control member 36 for positioning the command members 30, 32. Cams 30c, 32c formed on the command members 30, 32 cooperate with camways 36c formed on the control member 36, known in the state of the art, to:

- allow the command members 30, 32 to pivot when they move forward in the control member 36, and
- activate or deactivate clutch means 38 allowing the usual operation of the automatic injection device 13.

The control member 36 has a generally tubular shape.

An end sleeve 40 is fixed to the distal end of the control member 36. The end sleeve 40 is provided with a distal surface 42 intended to come into contact with the patient's skin.

Two locking elements 44, shown in particular on FIG. 3, are mounted so as to slide substantially radially in two slots 46 formed in the end sleeve 40 so as to form a membrane. As an alternative, more than two locking elements can be used. Each locking element 44 is provided, at its end closest to the X axis, with a limit stop 48 partly defined by a convex surface 50 of this locking element 44. These locking elements 44 slide substantially radially between two configurations:

a configuration permitting the passage of the cap for protecting the injection syringe 14, in which configuration the limit stops 48 are moved away from each other so that the separation between the two limit stops 48 is sufficient to permit the passage of the cap for protecting the injection syringe 14, a configuration permitting the immobilisation of the injection syringe 14, in which configuration the limit stops 48 are moved towards each other so that the space between the two limit stops 48 is small enough to hold the injection syringe 14 axially by its distal shoulder 24.

Thus, when the locking elements 44 are in their position permitting the passage of the cap for protecting the injection syringe 14, the injection syringe 14 can be positioned in the automatic injection device 13 without the protective cap interfering with the limit stops 48 of the locking elements 44. Similarly, when the locking elements 44 are in their immobilisation configuration, the injection syringe 14 is held axially when the injection needle 18 is inserted into the patient's skin.

The control member 36 is mounted telescopically inside an outer casing 52. Note that the control member 36 projects from the distal end of the outer casing 52. The outer casing 52 is intended to be grasped by its proximal end by the user. The relative movement of the outer casing 52 with respect to the control member 36 controls the actuation of the automatic injection device 13. In the initial configuration of the automatic injection device 13, the outer casing 52 and the control member 36 are axially moved away from each other, in other words the control member 36 is in its most distal position relative to the outer casing 52.

To actuate the automatic injection device 13, the user presses the distal end of the end sleeve 40 on the injection area and presses the automatic injection device 13 briefly against this area. Thus, the control member 36 retracts into the outer casing 52 and means for actuating the device 54, carried by one of the command members 32 and the control member 36, cooperate to actuate the automatic injection device 13.

A ramp 56 is formed in the part farthest away from the X axis of each locking element 44. When the automatic injection device 13 is actuated, these ramps 56 cooperate with the distal end of the outer casing 52, thereby moving the locking elements 44 from their position in which the injection syringe 14 is released to their position in which it is immobilised.

Two pins 58 are mounted slidably in the distal part of the control member 36. Each pin 58 cooperates with a proximal surface 60 of a locking element 44. Two hollows 62 are formed in each proximal surface 60 so that the pins 58 are housed in the hollows 62 when the locking elements 44 are in their passage or immobilisation configuration. Return means 64, for example return springs or any other equivalent element, force the pins 58 to press against the proximal surfaces 60 of the locking elements 44. Thus, when the locking elements 44 are in their passage or immobilisation configuration, a force is required to initiate the movement of these locking elements 44. In other words, the pins 58, by cooperating with the proximal surfaces 60 of the locking elements 44, create hard points retaining the locking elements 44 in their passage or immobilisation configuration.

The return springs 64 of the pins 58 are housed between shoulders 66 formed on the pins 58 and surfaces 68 formed on two members 70 for guiding the syringe support 28. Thus, the return springs 64 of the pins 58 return the syringe support 28 towards the proximal end of the control member 36. Thus, when the piston rod 26 and the syringe support 28 are released axially from the command members 30, 32, the return springs 64 of the pins 58 move the syringe support 28 towards the proximal end of the control member 36 and the injection needle 18 therefore retracts into the automatic injection device 13.

The control member 36 is provided with non-return locking means 72 at its proximal end. These non-return locking means 72 comprise two tabs 74 projecting radially from the control member 36. These tabs 74 are intended to cooperate with notches 76 formed in the outer casing 52. Each tab 74 can cooperate with three notches 76 aligned axially. Consequently, there are three pairs of notches 76 distributed axially, each pair of notches being able to cooperate with the pair of tabs 74. The tabs 74 are provided with distal limit stops 78 which prevent the control member 36 from sliding towards the distal end of the outer casing 52 when they cooperate with the notches 76 of the outer casing 52. In addition, the tabs 74 are inclined so that they can deform elastically by making the surfaces 80 of these tabs 74 cooperate with the notches 76 of the outer casing 52. Thus, when the control member 36 moves towards the proximal end of the outer casing 52, the tabs 74 retract radially and do not obstruct this movement.

Thus, the control member 36 and the outer casing 52 can be positioned relative to each other in three different positions, depending on which one of the three pairs of notches 76 of the outer casing 52 the tabs 74 of the control member 36 cooperate with. These three configurations are:

an initial position, in which the outer casing 52 and the control member 36 are axially moved away from each other; in this position, the locking elements 44 are in their passage position and the automatic injection device 13 is not actuated;

an intermediate position, in which the locking elements 44 are in their position immobilising the injection syringe 14 but the automatic injection device 13 is not actuated;

an actuation position, in which the outer casing 52 and the control member 36 are axially moved towards each other; in this position, the locking elements 44 are in their position immobilising the injection syringe 14 and the automatic injection device 13 is actuated.

FIGS. 5 to 12 show the automatic injection device 13 in several configurations corresponding to several steps of its operation.

Figure 5:
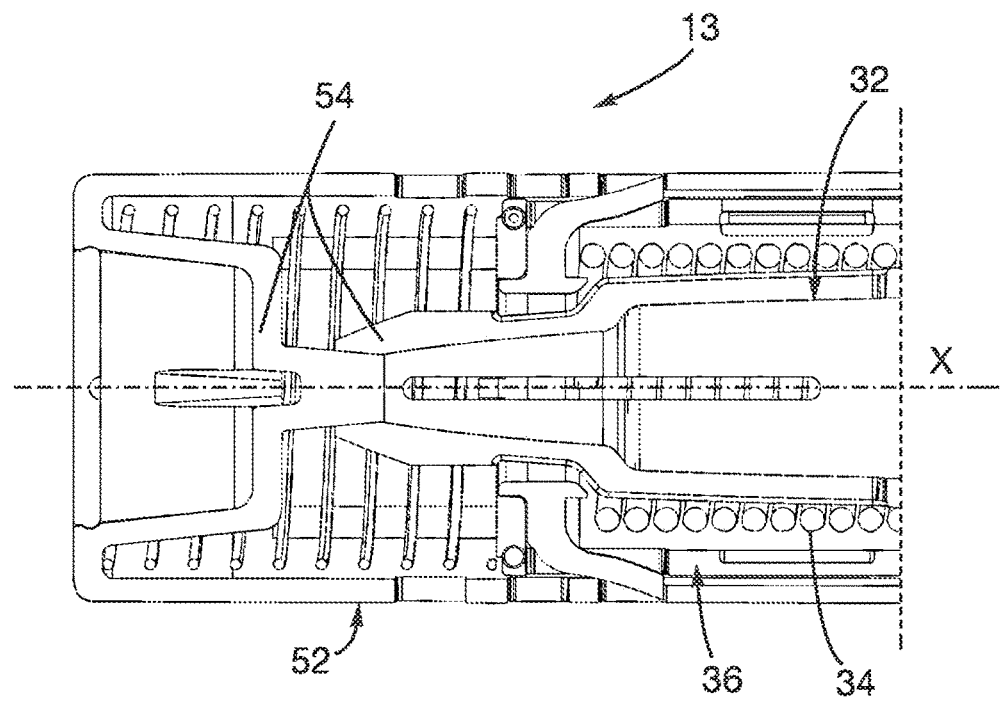
FIGS. 5 and 6 are detail views respectively V and VI of FIG. 4.
Figure 6:
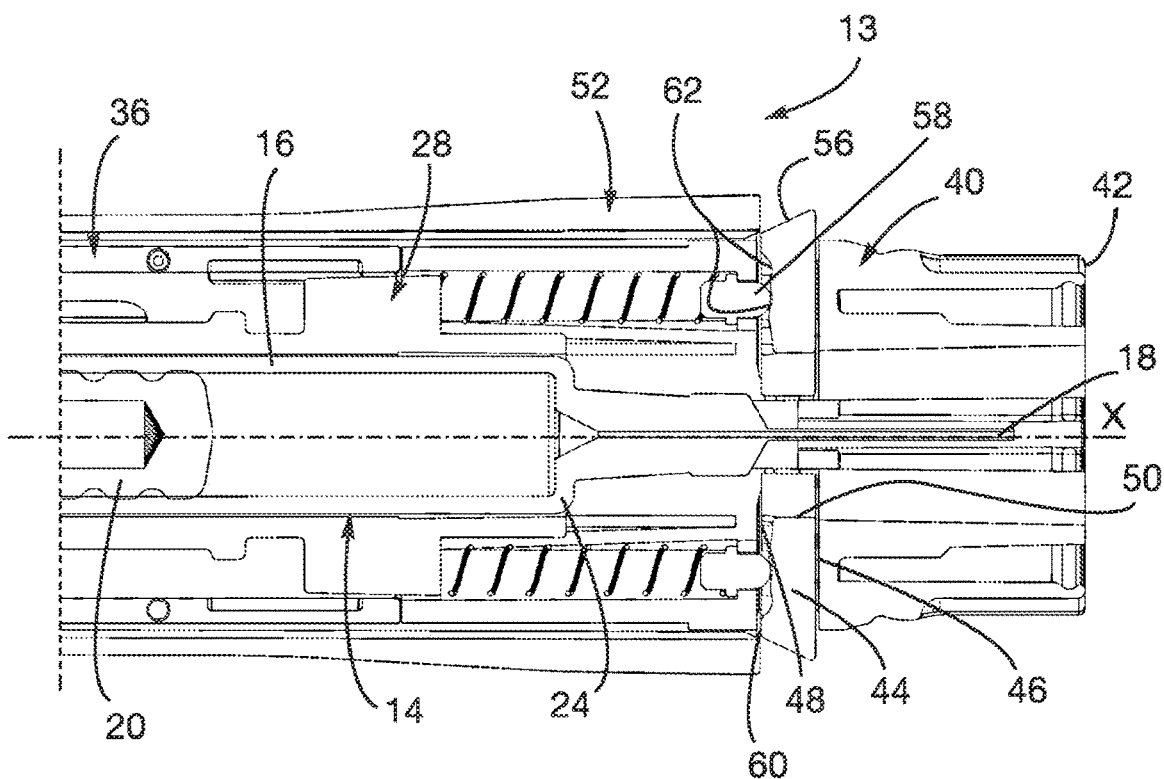

FIGS. 5 and 6 show the initial configuration of the automatic injection device 13, after removing the cap for protecting the injection needle 14. In this configuration, the locking elements 44 are in their passage configuration and the control member 36 is in its initial position relative to the outer casing 52.

Figure 7:
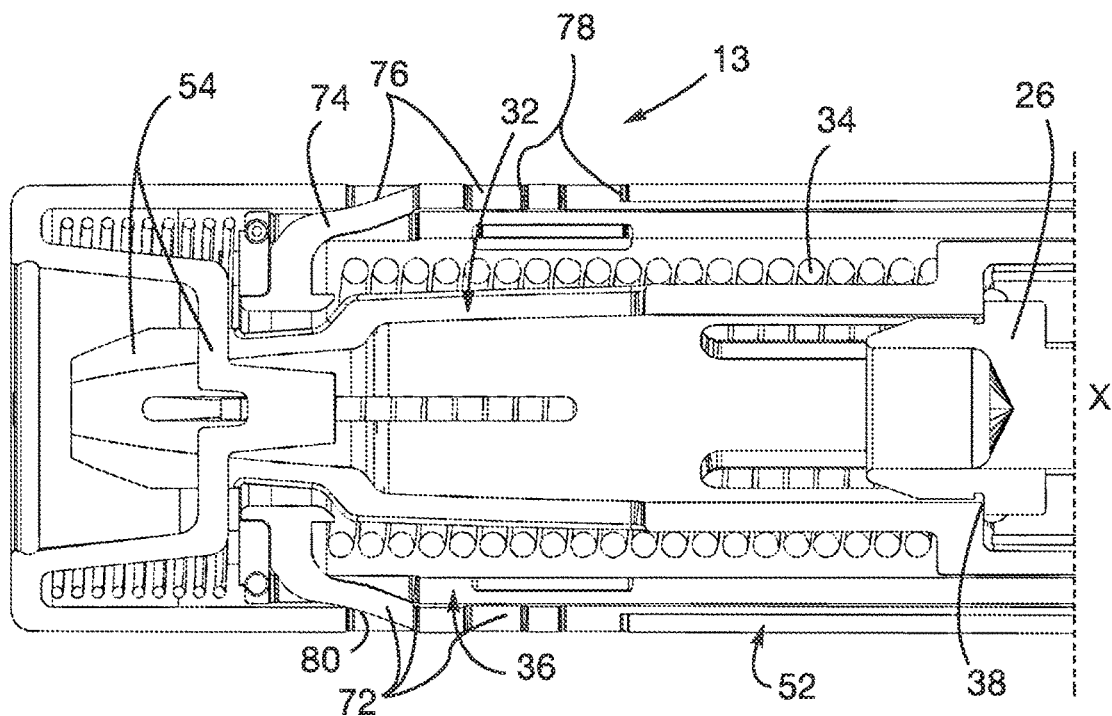
FIGS. 7 and 8, 9 and 10 and 11 and 12 are detail views similar to FIGS. 5 and 6, of the injection device in various operating configurations, in particular.
Figure 8:
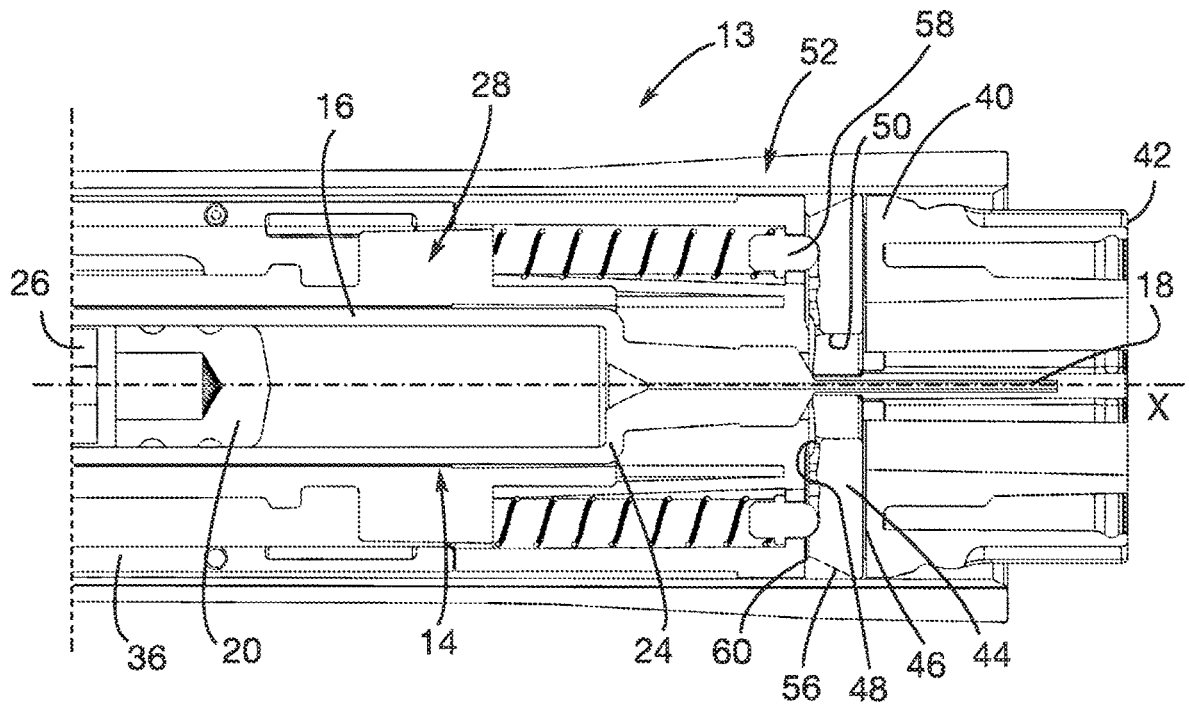

FIGS. 7 and 8 show the configuration for actuating the automatic injection device 13. In this configuration, the locking elements 44 are in their configuration for locking the injection syringe 14. The control member 36 is in its actuation position relative to the outer casing 52. The tabs 74 of the control member 36 cooperate with the most proximal notches 76 of the outer casing 52. The outer casing 52 and the control member 36 are immobilised relative to each other in the remainder of the operation of the automatic injection device 13.

Figure 9:
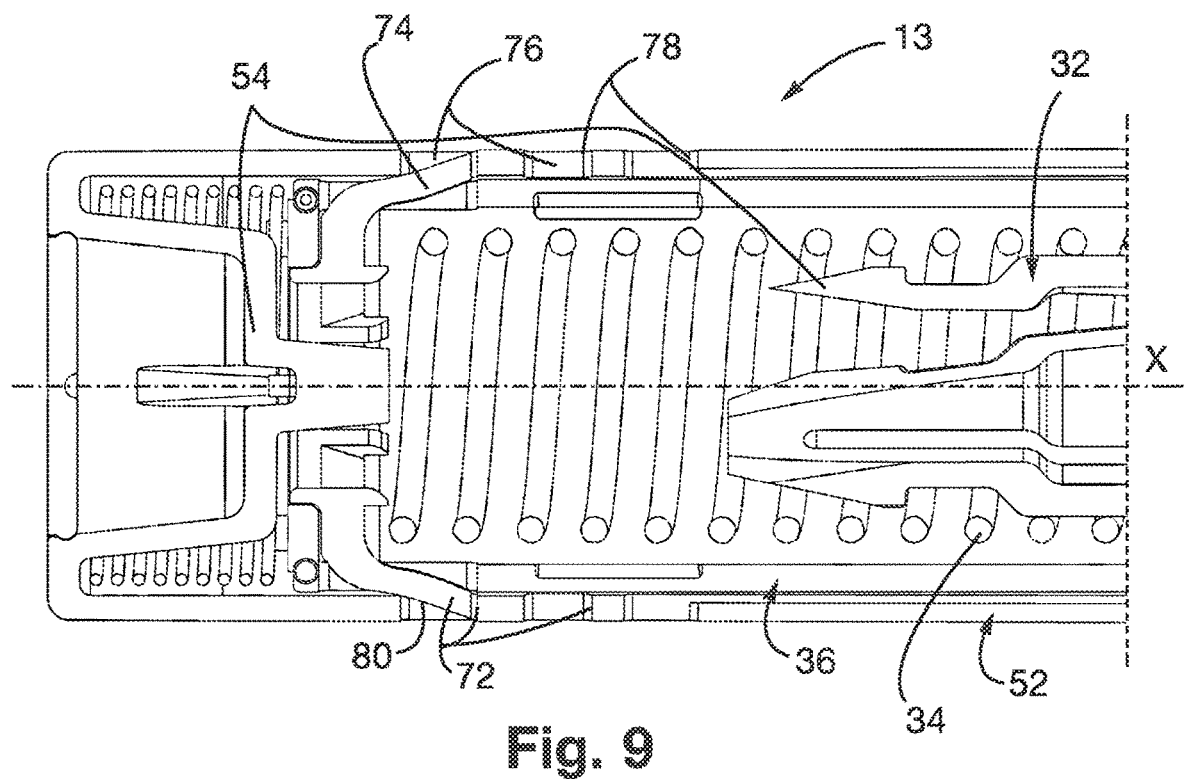
Figure 10:
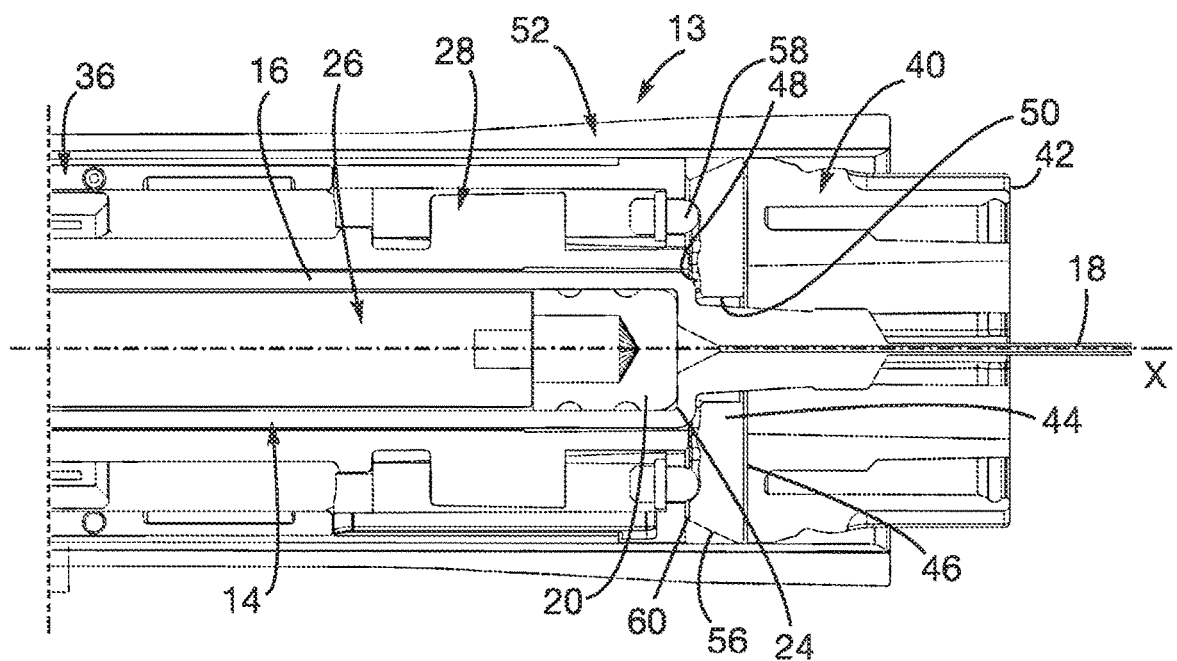

FIGS. 9 and 10 show the configuration at the end of injection of the automatic injection device 13. In this configuration, the distal shoulder of the injection syringe 14 is pressed against the limit stops 48 of the locking elements 44. The injection needle 18 is inserted into the patient's skin and the piston 20 abuts in the distal part of the syringe body 16.

Figure 11:
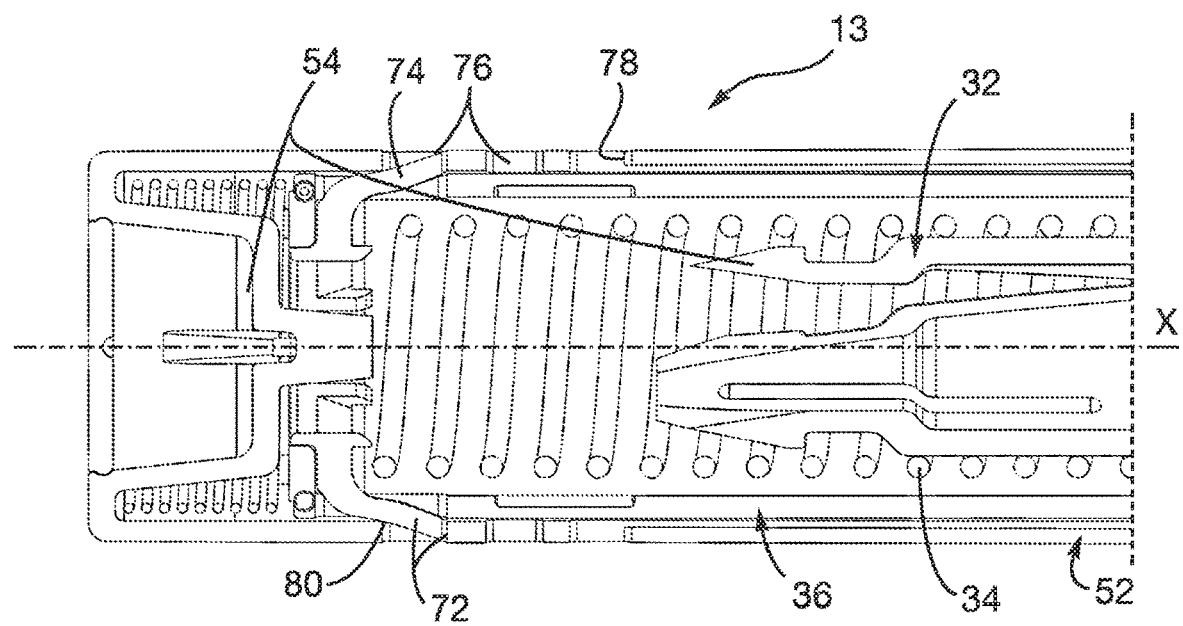
Figure 12:
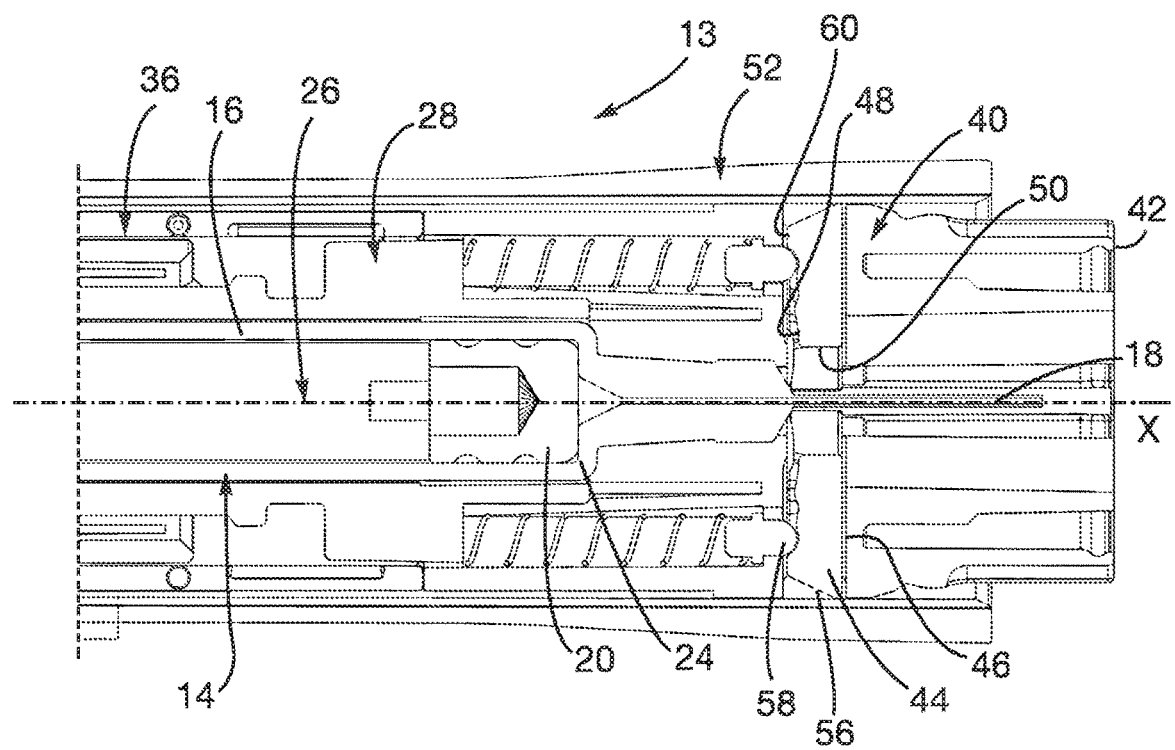

FIGS. 11 and 12 show the automatic injection device 13 after use. In this configuration, the syringe support 28 is returned axially towards the proximal part of the control member 36. The injection needle 18 is extracted from the patient's skin and no longer projects with respect to the end sleeve 40.

Figure 13:
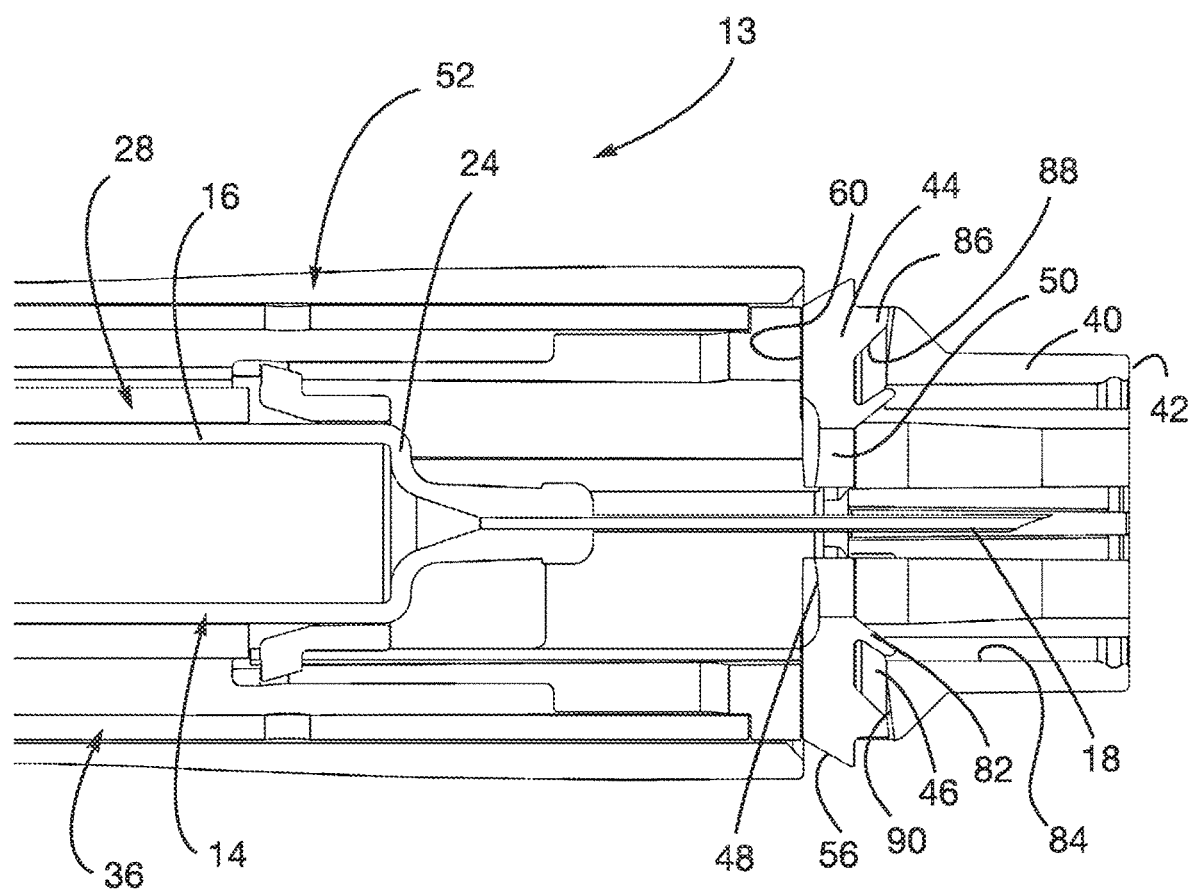
FIG. 13 is a cross-sectional view of the front part of an automatic injection device according to a second embodiment.

FIG. 13 shows an automatic injection device 13 according to a second embodiment of the invention. In this embodiment, the elements similar to those of the first embodiment are designated by the same references.

In this embodiment, the automatic injection device 13 does not comprise pins cooperating with the proximal surfaces 60 of the locking elements 44. Instead of these pins, the locking elements 44 are provided with flexible non-return tabs 82 which cooperate with an inner surface 84 of the end sleeve 40 as to prevent the locking elements 44 from being withdrawn. These flexible non-return tabs 82 prevent the locking elements 44 from moving radially outwards, so that the locking elements 44 cannot be completely separated from the rest of the automatic injection device 13.

In addition, each locking element 44 is provided with a projection 86 comprising a projecting surface 88 of the locking element 44. This projecting surface 88 is intended to cooperate with a complementary surface 90 of the end sleeve 40 so as to rub against this complementary surface 90 when the locking element 44 moves radially towards the X axis. Thus, the locking element 44 cannot move prematurely, it can only move towards the X axis when it is subjected to a radial force, in particular when the ramp 56 of the locking element 44 cooperates with the outer casing 52.

The invention is not limited to the embodiments described and other embodiments will be clearly apparent to those skilled in the art. In particular, more than two locking elements or a single locking element can be used. In addition, the injection syringe can be replaced by a cartridge provided with a needle.

The invention claimed is:

1. An automatic injection device comprising:
   an end sleeve;
   a syringe support slidably mounted relative to the end sleeve, the syringe support configured to carry an injection syringe provided with an injection needle and with a cap for protecting the injection needle; and
   a membrane formed by at least two locking elements which are mounted so as to slide substantially radially in the end sleeve between a configuration permitting passage of the cap for protecting the injection syringe, in which configuration limit stops formed on the at least two locking elements, intended to cooperate with a shoulder of the injection syringe, are moved away from each other, and a configuration permitting immobilization of the injection syringe, in which configuration the limit stops of the at least two locking elements are moved towards each other;
   wherein, when the at least two locking elements are in the configuration permitting the passage of the cap for protecting the injection syringe, the injection syringe is configured to be positioned in the automatic injection device with the cap going through a free space defined by the at least two locking elements, without the cap interfering with the limit stops of the at least two locking elements.

2. The automatic injection device according to claim 1, wherein the at least two locking elements comprise flexible non-return tabs configured to prevent the at least two locking elements from being withdrawn from the automatic injection device by cooperating with the end sleeve.

3. The automatic injection device according to claim 1, wherein the at least two locking elements are provided with projecting surfaces configured to rub against complementary surfaces of the end sleeve to prevent the at least two locking elements from moving prematurely from the configuration permitting the passage of the cap for protecting the injection syringe to the configuration permitting the immobilization of the injection syringe.

4. The automatic injection device according to claim 1, wherein the end sleeve is fixed to a distal end of a control member of generally tubular shape, in which the syringe support slides, the control member being mounted telescopically in an outer casing, relative movement of the control member with respect to the outer casing controlling actuation of the automatic injection device.

5. The automatic injection device according to claim 4, wherein the at least two locking elements are provided with ramps configured to cooperate with the outer casing to move from the configuration permitting the passage of the cap for protecting the injection syringe to the configuration permitting the immobilization of the injection syringe.

6. The automatic injection device according to claim 4, wherein pins are mounted slidably in the control member, the pins being forced, by return members, to press on respective surfaces of the at least two locking elements in which hollows are formed so as to create hard points retaining the at least two locking elements in the configuration permitting the passage of the cap for protecting the injection syringe or the configuration permitting the immobilization of the injection syringe.

7. The automatic injection device according to claim 6, wherein the return members are housed between respective surfaces of the syringe support and respective shoulders of the pins so as to elastically return the syringe support to a proximal end of the control member.

8. The automatic injection device according to claim 4, wherein the control member and the outer casing comprise non-return locking members, preventing the control member from sliding relative to the outer casing in one direction.

9. The automatic injection device according to claim 8, wherein the non-return locking members comprise a tab of the control member cooperating with notches formed in the outer casing.

10. The automatic injection device according to claim 1, wherein the limit stops of the at least two locking elements are partly defined by convex surfaces of the at least two locking elements.

11. The automatic injection device according to claim 1, wherein the syringe support carries the injection syringe which comprises a syringe body provided with a distal end carrying the injection needle, the shoulder of the injection syringe against which the limit stops of the at least two locking elements are intended to cooperate defining the distal end of the syringe body.

* * * * *